United States Patent
Amakawa et al.

(10) Patent No.: US 7,785,556 B2
(45) Date of Patent: Aug. 31, 2010

(54) METHOD OF RECOVERING AMMONIA

(75) Inventors: Kazuhiko Amakawa, Nigata (JP);
Fumio Tanaka, Nigata (JP); Takuji Shitara, Nigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 327 days.

(21) Appl. No.: 11/925,008

(22) Filed: Oct. 26, 2007

(65) Prior Publication Data

US 2008/0102014 A1    May 1, 2008

(30) Foreign Application Priority Data

Nov. 1, 2006  (JP)  .............. 2006-297483
Nov. 1, 2006  (JP)  .............. 2006-297484

(51) Int. Cl.
*C01C 1/10* (2006.01)
*C01C 1/12* (2006.01)
*C07D 333/38* (2006.01)

(52) U.S. Cl. ............... 423/352; 423/358; 423/369; 549/61; 549/474; 558/318; 558/329; 558/411; 558/421

(58) Field of Classification Search ............... 423/352, 423/358; 549/61, 474; 558/318, 329, 411, 558/421

See application file for complete search history.

(56) References Cited

U.S. PATENT DOCUMENTS 4,060,389 A    11/1977    Nishimura et al.
4,148,865 A    4/1979    Gelbein et al.
6,284,893 B2 *    9/2001    Shitara et al. ............... 546/286
2002/0001555 A1 *    1/2002    Benderly et al. ............. 423/238
2002/0146363 A1 *    10/2002    Benderly et al. ............. 423/352

FOREIGN PATENT DOCUMENTS

EP    1 113 001 A    7/2001
EP    1 160 199 A    12/2001
EP    1 247 781 A2    10/2002

(Continued)

OTHER PUBLICATIONS

Esp@cenet patent family data for corresponding EP appl'n. No. 07118994. Visited Nov. 9, 2009 at http://v3.espacenet.com/publicationDetails/biblio?DB=EPODOC&adjacent=true&locale=en_EP&FT=D&date=20080514&CC=EP&NR=1921043A1&KC=A1.*

(Continued)

*Primary Examiner*—Timothy C Vanoy
*Assistant Examiner*—Daniel Berns
(74) *Attorney, Agent, or Firm*—Antonelli, Terry, Stout & Kraus, LLP.

(57) ABSTRACT

A method of recovering ammonia by the distillation of an aqueous solution containing ammonia, carbon dioxide and hydrogen cyanide. The distillation is conducted using a distillation apparatus having at least its portion which comes into contact with the aqueous solution made of an alloy 1 or alloy 2. The alloy 1 contains 3% by weight or more of molybdenum, 15% by weight or more of nickel and 15% by weight or more of chromium. The alloy 2 contains 1% by weight or more of molybdenum, 9% by weight or less of nickel and 20% by weight or more of chromium. The use of the alloy 1 or alloy 2 prevents the corrosion of the distillation apparatus and enables the stable recovery of ammonia for a long period of time.

14 Claims, 1 Drawing Sheet

FOREIGN PATENT DOCUMENTS

GB      1 153 107 A     5/1969
GB      1 333 544 A     10/1973

OTHER PUBLICATIONS

Esp@cenet patent family data for EP 1247781. Visited Nov. 9, 2009 at http://v3.espacenet.com/inpadoc?DB=EPODOC&Iocale=en_EP&FT=D&CC=EP&NR=1247781A2&KC=A2.*

Internet Archive page, circa Feb. 13, 2004 of www.oceanint.com page. Visited Nov. 9, 2009 at http://www.web.archive.org/20040213013913/www.oceanint.com/content/materials/duplex/.*

The Engineering ToolBox, "Solubility of Gases in Water." (2005) Visited Nov. 12, 2009 at http://www.engineeringtoolbox.com/gases-solubility-water-d_1148.html.*

Extended European Search Report; Application No. EP 07 11 8994; Date: Apr. 8, 2008.

* cited by examiner

METHOD OF RECOVERING AMMONIA

BACKGROUND OF THE INVENTION

1. Field of the Invention

The present invention relates to a method of recovering ammonia by the distillation of an aqueous solution containing ammonia, carbon dioxide, and hydrogen cyanide.

2. Description of the Prior Art

Aromatic nitrites are useful as the raw material for the production of synthetic resins, agricultural chemicals, etc. and the intermediate material for amines, isocyanates, etc. Heterocyclic nitrites are useful as the intermediate material for medicines, feed additives, food additives, etc. The reaction of a cyclic hydrocarbon or heterocyclic compound each having an organic substituent with ammonia in the presence of an oxygen-containing gas is called ammoxidation. The nitrile compounds are generally produced by a vapor-phase catalytic ammoxidation. It is well known in the art to conduct the ammoxidation in the presence of a catalyst containing vanadium, molybdenum, iron, etc. For example, JP 11-209332A discloses the production of nitrile compounds by the ammoxidation of alkyl-substituted cyclic hydrocarbons or heterocyclic compounds in the presence of a catalyst containing V—Cr—B—Mo oxide. JP 9-71561A discloses the production of dicyanobenzene by the ammoxidation of xylene in the presence of a catalyst containing Fe—Sb—V oxide.

To produce the aromatic nitrile and heterocyclic nitrile in high yields, ammonia is used in excess of its theoretical amount in these methods. In the ammoxidation of alkyl-substituted cyclic hydrocarbons or heterocyclic compounds, ammonia is used 1.5 to 10 times the molar amount of the alkyl group. To produce the aromatic nitrites or heterocyclic nitrites with low costs, therefore, it is required to recover the non-reacted ammonia from the gas which remains after separating the nitrile compounds from the reaction product gas and recycle the recovered ammonia to the reaction system.

To recover the non-reacted ammonia from the remaining gas after separating the nitrile compounds form the ammoxidation product gas and recycle the recovered ammonia to the reaction system, the non-reacted ammonia is absorbed by water and ammonia is recovered from the obtained solution by distillation in known methods.

For example, "Hydrocarbon Processing," February 1976, pp. 103-106 describes the production of aromatic nitrile by the vapor-phase, catalytic oxidative ammonolysis in a fluidized bed manner in the presence of a catalyst containing a metal oxide. In the proposed method, the reaction product gas is cooled by a cooler to collect the nitrile compound. Thereafter, the remaining gas is introduced to an absorber where the non-reacted ammonia and the by-produced hydrogen cyanide are dissolved in water to separate from the waste gas (carbon monoxide, nitrogen, etc.). The resultant aqueous solution is introduced to a stripper where it is separated into a waste water containing high-boiling substances and a distillate containing ammonia, hydrogen cyanide, water, etc. The distillate was fed to a distillation tower where ammonia and an aqueous solution containing hydrogen cyanide and ammonium carbonate are separated from each other. The aqueous solution was separated into hydrogen cyanide/carbon dioxide gas and ammonia/water. The ammonia/water is returned to the distillation tower at the preceding stage.

"Chemical Engineering," November 1971, pp. 53-55 discloses a process of producing isophthalonitrile. In the proposed process, the ammoxidation of m-xylene with ammonia and air is performed in a fixed bed reactor in the presence of a catalyst containing vanadium oxide. The reaction product gas is introduced to a scrubber, where the gas is cooled to crystallize isophthalonitrile. The remaining gas is introduced to an absorber where the non-reacted ammonia and the by-produced hydrogen cyanide are dissolved in water. Waste gas from the top of absorber is sent to incineration. It is described that the ammonia recovered from the aqueous solution from the scrubber and absorber is recycled to the reaction system. However, the document is completely silent about the details thereof.

The inventors have proposed in JP 2001-348370A a method of producing a nitrile compound by the reaction between a cyclic hydrocarbon or heterocyclic compound each having an organic substituent, ammonia and an oxygen-containing gas. In the proposed method, the nitrile compound is separated from the reaction product gas and the non-reacted ammonia and by-produced hydrogen cyanide in the gas remaining thereafter are absorbed by water. The obtained aqueous solution is distilled under a pressure of 0.2 to 0.7 MPa to recover ammonia and hydrogen cyanide, which are then returned to the reaction system.

None of the above documents describe the corrosive properties of an aqueous solution containing ammonia, carbon dioxide and hydrogen cyanide nor the materials for the portion of a distillation apparatus which comes into contact with the aqueous solution.

"Table of Corrosion Resistance of Material for Chemical Apparatus," revised and enlarged edition, Kagaku Kogyo Sha, Co., Ltd. 1984, pp. 83, 88, 91 describes the corrosive properties of an aqueous solution of ammonium carbonate (ammonia-carbon dioxide-water mixture), ammonia water, and hydrogen cyanide, respectively. In this document, these corrosive properties are rated as Corrosion Degree A, namely, the corrosive properties against which a general purpose stainless steel such as SUS304 (austenitic stainless steel known as 18-8 stainless) can sufficiently resist.

SUMMARY OF THE INVENTION

The inventors studied the distillation of an aqueous solution containing ammonia, carbon dioxide and hydrogen cyanide, which had been obtained by separating the nitrile compound from the ammoxidation product gas and allowing ammonia, carbon dioxide and hydrogen cyanide in the gas remaining thereafter to be absorbed by water. It was found that materials such as SUS304 were severely corroded during the distillation, and the long-term production using a distillation apparatus made of such materials is industrially impossible.

In view of the problems in the art, the present invention has been made to remove the disadvantage due to the corrosion of distillation apparatus. Thus, an object of the present invention is to provide a method of recovering ammonia capable of conducting for a long period of time, which includes the separation of a nitrile compound from an ammoxidation product gas, the absorption of ammonia, carbon dioxide and hydrogen cyanide in the gas remaining thereafter by water, and the distillation of the obtained aqueous solution.

As a result of extensive research, the inventors have found that the above object is achieved by using a distillation apparatus having its portion which comes into contact with the aqueous solution made of a specific alloy. The present invention is based on this finding.

Thus, the present invention provides a method of recovering ammonia from an aqueous solution containing ammonia, carbon dioxide and hydrogen cyanide, which includes a step of distilling the aqueous solution using an distillation apparatus in which at least a portion being brought into contact with the aqueous solution is made of an alloy 1 composed of 3% by weight or more of molybdenum, 15% by weight or more of nickel and 15% by weight or more of chromium, or an alloy 2 composed of 1% by weight or more of molybdenum, 9% by weight or less of nickel and 20% by weight of chromium.

The present invention further provides a method of producing a nitrile compound which includes a step of allowing a cyclic hydrocarbon or a heterocyclic compound each having at least one organic substituent to react with ammonia to obtain a reaction product gas; a step of separating the nitrile compound from the reaction product gas; a step of allowing ammonia, carbon dioxide and hydrogen cyanide in a remaining gas to be absorbed by water; and a step of recovering ammonia by the method as described above.

DETAILED DESCRIPTION OF THE INVENTION

Figure 1:
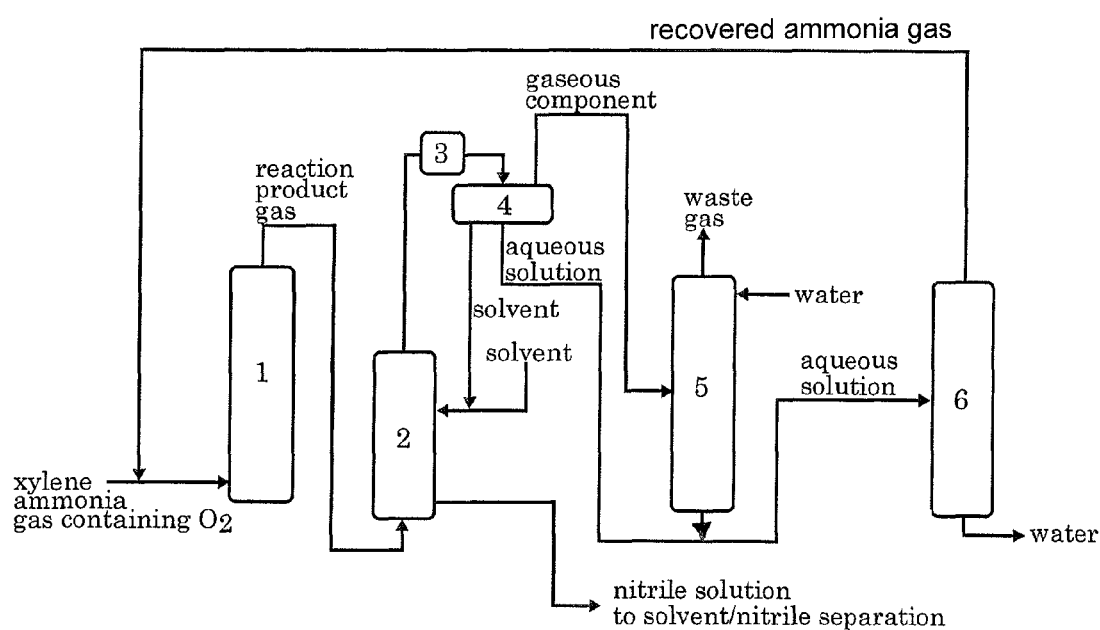
FIG. 1 is a schematic illustration of the process flow of the present invention for producing nitrile compounds.

In the present invention, nitrile compounds are produced by the vapor-phase catalytic ammoxidation. The ammoxidation can be carried out by any of known methods. Generally, the nitrile compound is produced by bringing a cyclic hydrocarbon or heterocyclic compound, ammonia, and an oxygen-containing gas into contact with a vapor-phase ammoxidation catalyst. In some kinds of catalyst, the ammoxidation is performed in the absence of molecular oxygen. Since the oxygen in the catalyst is consumed in the ammoxidation in the absence of molecular oxygen, the catalyst after used in the ammoxidation is oxidized in an oxygen-containing gas for regeneration, thereby being reused in the next ammoxidation. The ammoxidation may be performed in any of a fixed bed manner, a moving bed manner and a fluidized bed manner. In the present invention, any of catalysts may be used without particular limitation as long as they are the ammoxidation catalysts suitable for the vapor-phase catalytic reaction. Preferred are, for example, catalysts which contain an oxide of at least one element selected from vanadium, molybdenum, iron, manganese and tungsten.

The cyclic hydrocarbon having at least one, preferably 1 to 3 organic substituents, which is used in the present invention, has a carbon ring such as benzene, naphthalene, anthracene, cyclohexene, cyclohexane, dihydronaphthalene, tetralin and decalin and has at least one organic substituent on the carbon ring such as methyl group, ethyl group, propyl group, formyl group, acetyl group, hydroxymethyl group and methoxycarbonyl group. The cyclic hydrocarbon may be further substituted by a group inert to the ammoxidation such as halogen group, hydroxyl group, alkoxyl group, phenyl group, amino group and nitro group. Examples of the cyclic hydrocarbon having at least one organic substituent include toluene, xylene, trimethylbenzene, ethylbenzene, methylnaphthalene, dimethylnaphthalene, methyltetralin, dimethyltetralin, chlorotoluene, dichlorotoluene, methylaniline, cresol and methylanisole.

The heterocyclic compound having at least one, preferably 1 to 3 organic substituents, which is used in the present invention, has a heterocyclic ring such as furan, pyrrole, indole, thiophene, pyrazole, imidazole, oxazole, pyran, pyridine, quinoline, isoquinoline, pyrroline, pyrrolizine, imidazoline, imidazolidine, piperidine, and piperazine and has at least one organic substituent mentioned above on the heterocyclic ring. Like the cyclic hydrocarbon, the heterocyclic compound may be further substituted by the group inert to the ammoxidation. Examples of the heterocyclic compound having at least one organic substituent include furfural, 2-methylthiophene, 3-methylthiophene, 2-formylthiophene, 4-methylthiazole, methylpyridine, dimethylpyridine, trimethylpyridine, methylquinoline, methylpyrazine, dimethylpyrazine, and methylpiperazine.

These compounds may be used alone or in combination of two or more. By allowing these compounds to react with ammonia, the organic substituent is converted to cyano group, thereby obtaining a corresponding nitrile compound. The present invention is suitably applied particularly to the production of dicyanobenzene from xylene.

Industrial grade ammonia may be used in the present invention. The molar ratio of ammonia to be used and the organic substituent in the starting cyclic hydrocarbon or heterocyclic compound ($NH_3$/organic substituent) is preferably from 1.5 to 10, more preferably from 3 to 7. By using ammonia in excess of the theoretical amount, the yield of the nitrile compound increases. The non-reacted ammonia is recovered for reuse. When the amount of ammonia to be used is within the above range, the reduction of the yield of the nitrile compound is avoided, and the loss of the non-reacted ammonia and the increase in the recovery costs can be prevented.

Air is generally used as the oxygen-containing gas. If necessary, oxygen may be enriched by the addition of pure oxygen, or an inert gas may be further added. The molar ratio of oxygen to be used and the organic substituent in the starting cyclic hydrocarbon or heterocyclic compound ($O_2$/organic substituent) is preferably from 1.5 to 7, more preferably from 1.5 to 5. Within the above range, the yield and the space time yield of the nitrile compound is good.

The ammoxidation is carried out at atmospheric pressure, under pressure, or at reduced pressure. Preferably, the ammoxidation pressure is from around atmospheric pressure to 0.3 MPaG. The contact time between the reactant gas and the catalyst is preferably from 0.1 to 50 s, although depending upon the kind of the compound having the organic substituent, the proportion of the stating materials to be fed, the kind of catalyst, and the reaction conditions such as temperature. The reaction temperature is preferably from 300 to 500° C., more preferably from 330 to 470° C. Within the above range, a sufficient reaction rate is obtained and the by-production of carbon dioxide and hydrogen cyanide is reduced, thereby increasing the yield of the nitrile compound. It is recommended to suitably select the reaction temperature so as to obtain an optimum yield, while taking the activity of catalyst under the above reaction conditions into consideration.

In the present invention, the produced nitrile compound is separated from the reaction product gas discharged from the ammoxidation reactor, while allowing ammonia, carbon dioxide and hydrogen cyanide in the reaction product gas to be absorbed by water. Then, the resultant aqueous solution is distilled. The absorption of ammonia, carbon dioxide and hydrogen cyanide in the reaction product gas by water is conducted by, but not limited to:

(1) a method in which the nitrile compound is absorbed to a solvent by bringing the reaction product gas with an organic solvent and then the remaining gas is brought into contact with water, thereby absorbing ammonia, carbon dioxide and hydrogen cyanide from the reaction product gas into water;

(2) a method in which the reaction product gas and water which are in contact with each other are cooled, thereby obtaining an aqueous solution containing ammonia, carbon dioxide and hydrogen cyanide, while separating a solid slurry of the nitrile compound (when the nitrile compound is solid under the cooling conditions) or an organic liquid phase containing the nitrile compound (when the nitrile compound is liquid hardly soluble to water under the cooling conditions); or (3) a method in which the reaction product gas is cooled to allow the nitrile compound to crystallize or condense into liquid, and then, after separating the crystals or liquid, the remaining gas is brought into contact with water to obtain an aqueous solution containing ammonia, carbon dioxide and hydrogen cyanide.

The composition of the aqueous solution thus obtained is preferably 5 to 50% by weight of ammonia, 0.1 to 5% by weight of hydrogen cyanide, 1 to 20% by weight of carbon dioxide, and a balance being substantially water. In some cases, the aqueous solution may contain a trace amount of organic substance such as nitrile compound remaining not separated. The composition may vary according to the amount of ammonia used and reaction results of the ammoxidation, the method of absorbing ammonia, carbon dioxide and hydrogen cyanide in the reaction product gas by water, the amount of water used in the absorption. The use of water in smaller amount is advisable in view of reducing the load of the distillation apparatus. However, an excessively small amount of water used may cause troubles such as the clogging of conduits because ammonium salts such as ammonium carbonate precipitate in the aqueous solution. Organic substances hardly soluble to water make the temperature and pressure of distillation apparatus variable, thereby making the distillation operation instable. Therefore, the concentration of these organic substances should be as low as 0.5% by weight or less. The organic substances hardly soluble to water are derived from the raw materials for the ammoxidation and the solvents for collecting the reaction products and nitrile compounds, and examples thereof include benzene, toluene, xylene, trimethylbenzene, benzonitrile, methylbenzonitrile, chlorobenzene, and anisole.

In the present invention, ammonia is recovered from the aqueous solution containing ammonia, carbon dioxide and hydrogen cyanide by distillation. The aqueous solution is obtained, for example, in the production of nitrile compound mentioned above, although not limited thereto. The distillation is performed by using an evaporating distillation column, a packed distillation column, or a plate distillation column, preferably using the packed distillation column. The packing materials generally used for stacked packing and dumped packing are usable. The distillation apparatus is equipped with instruments, such as a boiler and condenser, which are used in general distillation apparatus.

The aqueous solution is introduced to the distillation apparatus and distilled there for the separation. The distillation of the aqueous solution is performed preferably in a continuous manner, because the ammoxidation is performed generally in a continuous manner. Ammonia is recovered from the top of the distillation apparatus, while water is recovered from the bottom. Hydrogen cyanide and carbon dioxide are distributed to the top, bottom or both of the distillation apparatus according to the distillation conditions. To produce the nitrile compound at lower costs, it is recommended to recycle the ammonia-containing fraction from the top to the ammoxidation. The present invention is particularly suitable for the distillation to recover ammonia, hydrogen cyanide and carbon dioxide together from the top, while recovering water which is substantially free from ammonia, hydrogen cyanide and carbon dioxide from the bottom. Although the water recovered from the bottom is generally discarded, the recovered water may be partly or wholly reused for absorption of ammonia, carbon dioxide and hydrogen cyanide. If reused by recycling, the amount of waste water is largely reduced and the burden for the waste water treatment can be advantageously reduced.

The ammonia-containing gaseous component from the top of the distillation apparatus is cooled, preferably to 60 to 100° C. By avoiding excessive cooling to below 60° C., ammonium carbonate is prevented from precipitating as solid, thereby enabling the process to run without hindrance. By the cooling, the gas is condensed to a liquid. It is preferable to partially condense the gaseous distillate so as to discharge a part of distillate in a gaseous state rather than to completely condense. The gaseous component remaining after the partial condensation is rich in ammonia, and therefore, suitably recycled to the ammoxidation reactor as it is. The liquid component obtained by the partial condensation is refluxed into the distillation apparatus. In most cases, a part of the gas at the top of distillation apparatus remains not condensed to liquid when it is cooled to 60 to 100° C.

The distillation is performed preferably under pressure, more preferably under 0.1 to 0.7 MPaG and still more preferably under 0.2 to 0.5 MPaG. Within the above range, the continuous distillation is easy to perform for a long period of time. Within the above range, the production of side products attributable to the decomposed hydrogen cyanide in the distillation apparatus can be minimized. As a result, the reduction of distillation capacity due to foaming, flooding and scaling on heat exchanger is prevented. In addition, the discoloring and the increase in total oxygen demand of the water discharged from the bottom can be prevented. This facilitates the waste water treatment. Further, since the dew point of the top of distillation apparatus is not lowered, ammonium carbonate does not precipitate, thereby ensuring a stable distillation. Also, since the increase in the steaming load is avoided, the distillation capacity is not lowered, thereby preventing the reduction of the amount of aqueous solution being treated.

The distillation temperature varies depending upon the operation pressure, the composition of the aqueous solution, the composition of the products to be discharged from the top and bottom. The top temperature is preferably from 80 to 140° C. and more preferably from 90 to 120° C. The bottom temperature is preferably from 120 to 170° C. and more preferably from 130 to 160° C. The reflux ratio depends upon the composition of the aqueous solution to be distilled and the intended separation specification, and preferably from 0.1 to 2.0, more preferably from 0.2 to 1.5.

The portion of the distillation apparatus which comes into contact with the aqueous solution (hereinafter referred to as "liquid-contact portion") is formed from an alloy 1 or alloy 2 in its entirety or at least its surface, for example, a depth of 0.02 to 1 mm from the surface.

The alloy 1 contains 3% by weight or more of molybdenum, 15% by weight or more of nickel and 15% by weight or more of chromium. The content of molybdenum is preferably from 3 to 25% by weight, more preferably from 3.5 to 20% by weight. The content of nickel is preferably from 15 to 82% by weight, more preferably from 15 to 70% by weight. The content of chromium is preferably from 15 to 30% by weight, more preferably from 15 to 25% by weight.

The alloy 2 contains 1% by weight or more of molybdenum, 9% by weight or less of nickel and 20% by weight or more of chromium. The content of molybdenum is preferably from 1 to 10% by weight, more preferably from 2 to 8% by weight. The content of nickel is preferably from 0 to 9% by weight, more preferably from 0 to 8% by weight. The content of chromium is preferably from 20 to 40% by weight, more preferably from 20 to 30% by weight.

The alloying metals other than nickel, chromium and molybdenum include copper, aluminum, tungsten, cobalt, titanium, manganese, etc. and the balance of iron. The content of the alloying metals other than nickel, chromium, molybdenum and iron is preferably 14% by weight or less, more preferably 6% by weight or less (inclusive of zero) in total. The corrosion resistance decreases as the content of copper increases. Therefore, the content of copper is preferably 10% by weight or less, more preferably 5% by weight or less, and still more preferably 3% by weight or less. The content of carbon is as low as possible, preferably 0.08% by weight or less, and more preferably 0.03% by weight or less. The balance of iron is preferably from 40 to 70% by weight.

The alloy 1 is commercially available as, for example, Hastelloy C (Mitsubishi Materials Corporation), NAR-A (Sumitomo Metal Industries, Ltd.), NAR-B (Sumitomo Metal Industries, Ltd.), NAR-20-25-LMCu (Sumitomo Metal Industries, Ltd.), 2RK65 (Sandvik K.K.), NTK-M5 (Nippon Metal Industry Co., Ltd.). Their equivalents are also usable. Preferred are Hastelloy C (high nickel-content alloy) and its equivalents because of their high corrosion resistance.

The alloy 2 is preferably selected from alloys classified as ferritic stainless steels and duplex stainless steels. Examples thereof include standardized steels such as SUS329J1, SUS329J3L, SUS329J4L and SUS447J1; commercially available steels meeting the standards; and their equivalents.

The inventors have found that the liquid-contact portion, particularly the portion, such as plates and packing materials, at which evaporation and condensation are constantly repeated (referred to as "fractionating portion") is heavily corroded. Although not fully elucidate, the corrosion may be advanced at the fractionating portion by the physical shock attributable to the phase change due to evaporation and condensation or by the change in the composition of vapor phase and liquid phase. It has been not known that the evaporation of the aqueous solution containing ammonia, carbon dioxide and hydrogen cyanide significantly promotes the corrosion. The fractionating portion is particularly subject to the corrosion. However, it is difficult to make the fractionating portion sufficiently corrosion-resistant by selecting its structure. Therefore, it is quite effective to form the whole part or at least the surface of the liquid-contact portion, particularly the fractionating portion by the alloy 1 or alloy 2.

The corrosion of the liquid-contact portion is promoted as its temperature increases and the ammonia concentration increases. Particularly, the corrosion is severe when the temperature of the liquid-contact portion is 90° C. or high and the ammonia concentration is 2.7% by weight or more. The present invention is particularly effective for such conditions. Since the fractionating portion at the top and its vicinity of the distillation apparatus is frequently subject to such conditions, the fractionating portion should be formed from the alloy 1 or alloy 2.

The liquid-contact portion is not necessarily made of the alloy 1 or alloy 2 throughout the distillation apparatus. For example, the liquid-contact portion at the bottom may be formed from a general purpose stainless steel such as SUS304, SUS304L, SUS316 and SUS316L when the water discharged from the bottom has very low concentrations of ammonia, hydrogen cyanide and carbon dioxide.

The present invention is described in more detail with reference to the examples and comparative examples. However, it should be noted that the scope of the present invention is not limited thereto.

EXAMPLE 1

According to the process flow shown in FIG. 1, the ammoxidation, the separation of the nitrile compound, the contact of the remaining gas with water, and the distillation of the aqueous solution were conducted continuously. In FIG. 1, each reference numeral represents an ammoxidation reactor 1, a nitrile compound absorber 2, a cooler 3, a decanter 4, an ammonia absorber 5 and a distillation apparatus 6.

Ammoxidation

In accordance with the method described in JP 6-23158B, a silica-supported ammoxidation catalyst for fluidized bed was prepared. The catalyst contained 50% by weight of silica and V, Cr, Mo and B as the active components in a proportion of 1:1:0.1:0.2. The fluidized-bed ammoxidation reactor was packed with the catalyst. Then, the ammoxidation was conducted continuously while supplying a meta-para mixed xylene (m-xylene: 80% by weight, p-xylene: 20% by weight), ammonia, air, and the ammonia-containing distillate recovered from the distillation apparatus 6 into the ammoxidation reactor 1. The supplying amount (WHSV) of the mixed xylene was 0.07 h$^{-1}$, the ammonia/xylene molar ratio was 10, the molecular oxygen/xylene molar ratio was 5.5, the reaction temperature was 410° C., GHSV was 700 h$^{-1}$, and the pressure was 0.05 MPaG. The yield of dicyanobenzene (total of meta and para isomers) based on the raw xylene was 81 mol % immediately after starting the production.

Separation of Nitrile Compound

The reaction product gas from the ammoxidation reactor 1 was introduced into the bottom of the nitrile compound absorber 2. The absorber was a tower type and had an inlet for the reaction product gas and an outlet for discharging the absorbed liquid. In the central portion of the tower, metal packing materials were dumpedly packed. In the nitrile compound absorber 2, the reaction product gas was continuously brought into contact with an absorbing solvent (trimethylbenzene) which was fed from the top of the absorber 2. The temperature of the bottom of the absorber 2 was set at 140° C. From the top of the absorber 2, a gas composed of ammonia, hydrogen cyanide, carbon dioxide, nitrogen, oxygen, carbon dioxide, solvent, and non-reacted xylene was discharged. The discharge gas was cooled in the cooler 3 to 20° C. to condense the solvent and water partly. Thereafter, the gas was introduced to the decanter 4. In the decanter 4, the gas was condensed and the resultant solvent phase, water phase and gas phase were vapor-liquid and liquid-liquid separated. The gas phase from the decanter 4 was introduced to the ammonia absorber 5. The solvent phase was returned to the nitrile compound absorber 2. The water phase containing ammonia, hydrogen cyanide and carbon dioxide was combined with the aqueous solution form the ammonia absorber 5 and then introduced to the distillation apparatus 6 for distillation.

Absorption of Ammonia by Water

The gas from the decanter 4 was introduced to the ammonia absorber 5 and brought into contact with water to obtain an aqueous solution containing ammonia, hydrogen cyanide and carbon dioxide. The remaining gas containing nitrogen, oxygen, carbon dioxide, hydrogen cyanide, carbon monoxide, and ammonia was introduced to a device for treating waste gas.

Distillation of Aqueous Solution

The distillation apparatus 6 was a packed distillation tower having a condenser and reflux zone at its top portion and bumpedly packed with packing materials (cascade mini-rings). The liquid-contact portions of the body of tower and the packing materials were made of Hastelloy C22, the liquid-contact portion of the condenser and the reflux zone was made of NAR-A, and the liquid-contact portion of the bottom and reboiler was made of SUS316L. The elemental composition (catalogue values) of each alloy is shown in Table 1.

TABLE 1

| Alloy | Content (wt %) | | | | | | | | | | |
|---|---|---|---|---|---|---|---|---|---|---|---|
| | Cr | Ni | Mo | Cu | Co | W | Ti | Si | Mn | C | Fe |
| Hastelloy C22 | 22 | 57 | 13 | 0 | ≦2.5 | ≦3.5 | 0 | 0 | 0 | ≦0.02 | balance |
| NAR-A | 22 | 26 | 5 | 0 | 0 | 0 | 0.35 | 0 | 0 | 0 | balance |
| SUS316L | 17 | 12 | 2 | 0 | 0 | 0 | 0 | ≦1 | ≦2 | ≦0.03 | balance |

The aqueous solution fed to the upper plate of the distillation apparatus 6 contained 15.4% by weight of ammonia, 4.9% by weight of carbon dioxide, 1.3% by weight of hydrogen cyanide, small amount of organic impurities, and water (balance). The distillation was conducted under the conditions:

operation pressure: 0.32 MPaG bottom temperature: 148° C.

gas temperature at the top: 103° C.

outlet temperature of condenser: 81° C.

reflux ratio: 0.6.

The gas was partially condensed at the tower top. The gas remaining after the partial condensation was recycled to the ammoxidation reactor, and the liquid was refluxed. The gas remaining after the partial condensation (recovered ammonia gas) contained 60.7% by weight of ammonia, 26% by weight of carbon dioxide, 5.7% by weight of hydrogen cyanide and water (balance). The liquid at bottom was substantially water containing 0.02% by weight of ammonia. Carbon dioxide and hydrogen cyanide were not detected (detection limit: 2 ppm by weight).

The production of dicyanobenzene was continuously performed for about 300 days. Thereafter, the inside of the distillation apparatus was inspected. The reduction in thickness of the liquid-contact portion was less than 0.02 mm/year at any of the body portion, packing materials, condenser and reflux zone, showing substantially no corrosion. During about 300-day continuous production, the overall yield of dicyanobenzene (total of meta and para isomers) based on the raw xylene was 76 to 81 mol %, showing that the present invention enabled the stable, continuous production of dicyanobenzene by ammoxidation for a long period of time.

EXAMPLE 2

The procedure of Example 1 was repeated except that the liquid-contact portion of each of the body of tower, the packing materials, the condenser and the reflux zone was made of SUS329J4L (SAF2507 of Sandvik K.K.). The elemental composition (catalogue values) of SUS329J4L is shown in Table 2.

TABLE 2

| Alloy | Content (wt %) | | | | | | | | | | |
|---|---|---|---|---|---|---|---|---|---|---|---|
| | Cr | Ni | Mo | Cu | Co | W | Ti | Si | Mn | C | Fe |
| SUS329J4L | 25 | 7 | 3 | 0 | 0 | 0 | 0 | 0 | 0 | ≦0.03 | balance |

The production of dicyanobenzene was continuously performed for about 300 days. Thereafter, the inside of the distillation apparatus was inspected. The reduction in thickness of the liquid-contact portion was less than 0.02 mm/year at any of the body portion, packing materials, condenser and reflux zone, showing substantially no corrosion. During about 300-day continuous production, the overall yield of dicyanobenzene (total of meta and para isomers) based on the raw xylene was 76 to 81 mol %, showing that the present invention enabled the stable, continuous production of dicyanobenzene by ammoxidation for a long period of time.

COMPARATIVE EXAMPLE 1

The recovery of ammonia was conducted continuously in the same manner as in Example 1 except that the liquid-contact portion of each of the body of tower, the packing materials, the condenser and the reflux zone was made of SUS316L. After about 180 days, the separation capacity was reduced and the temperature distribution in the distillation tower was changed. Therefore, the process was discontinued and the inside of the distillation tower was inspected. The packing materials were corroded throughout the surface, and the appreciable reduction in thickness and the change of shape were found. In addition, the deposition of the packing materials in layer, which was attributable to the change of their shape, was found. The corrosion speed was 0.2 mm/year when calculated from the reduction in the weight of the packing materials in the uppermost portion of the packed layer. The liquid-contact portion of the body of tower was similarly corroded throughout its surface. Thus, it was impossible to continue the process further.

EXAMPLES 3-12 and COMPARATIVE EXAMPLES 2-7

Each exposure test was conducted in the same manner as in Example 1 except for disposing test pieces with a shape of plate made of different material on the dumped layer of packing materials. The elemental compositions (catalogue values) of the materials for the test pieces are shown in Table 3.

After about 300 days of the continuous operation, the test pieces were taken out of the distillation apparatus. The corrosion speed was calculated from the reduction in the weight of test pieces. The results are shown in Table 3.

TABLE 3

| | Alloy | Content (wt %) | | | | | | | | | | | Corrosion Speed (mm/year) |
|---|---|---|---|---|---|---|---|---|---|---|---|---|---|
| | | Cr | Ni | Mo | Cu | Co | W | Ti | Si | Mn | C | Fe | |
| Examples | | | | | | | | | | | | | |
| 3 | NAR-A | 22 | 26 | 5 | 0 | 0 | 0 | 0.35 | 0 | 0 | 0 | balance | 0.018 |
| 4 | NAR-B | 25 | 50 | 6 | 1 | 0 | 0 | 1 | 0 | 0 | 0 | balance | 0.008 |
| 5 | NAR-20-25LMCu | 20 | 25 | 5 | 2 | 0 | 0 | 0 | 0 | 0 | 0 | balance | 0.021 |
| 6 | Hastelloy C-276 | 16 | 56 | 16 | 0 | 0 | 4 | 0 | 0 | 0 | 0 | balance | 0.001 |
| 7 | Hastelloy C-22 | 22 | 57 | 13 | 0 | ≦2.5 | ≦3.5 | 0 | 0 | 0 | ≦0.02 | balance | 0.001 |
| 8 | 2RK65 | 20 | 25 | 5 | 2 | 0 | 0 | 0 | 0 | 0 | 0 | balance | 0.039 |
| 9 | NTK-M5 | 18 | 16 | 5 | 0 | 0 | 0 | 0 | 1 | 2 | ≦0.02 | balance | 0.032 |
| 10 | SUS329J4L | 25 | 7 | 3 | 0 | 0 | 0 | 0 | 0 | 0 | ≦0.03 | balance | 0.010 |
| 11 | SUS329J3L | 22 | 5 | 3 | 0 | 0 | 0 | 0 | 0 | 0 | ≦0.02 | balance | 0.035 |
| 12 | SUS447J1 | 30 | <0.6 | 2 | 0 | 0 | 0 | 0 | 0 | 0.4 | ≦0.01 | balance | 0.001 |
| Comparative Examples | | | | | | | | | | | | | |
| 2 | SUS316L | 17 | 12 | 2 | 0 | 0 | 0 | 0 | ≦1 | ≦2 | ≦0.03 | balance | 0.219 |
| 3 | NAR-20-3 | 20 | 33 | 2 | 3 | 0 | 0 | 0 | 2 | 0.2 | 0.1 | balance | 0.255 |
| 4 | Hastelloy B | 0 | 66 | 27 | 0 | 0 | 0 | 0 | 0 | 0 | 0.3 | balance | 0.400 |
| 5 | Monel | 0 | 65 | 0 | 34 | 0 | 0 | 0 | 0.5 | 2 | 0.3 | balance | >1 |
| 6 | Carpenter 20 | 20 | 30 | 2 | 3 | 0 | 0 | 0 | 0 | 1.5 | ≦0.07 | balance | 0.120 |
| 7 | pure Ti | 0 | 0 | 0 | 0 | 0 | 0 | balance | 0 | 0 | 0 | ≦0.5 | 0.340 |

NAR-20-3: available from Sumitomo Metal Industries, Ltd.
SUS329J4L: DP-3 available from Sumitomo Metal Industries, Ltd.
SUS329J3L: SAF2205 available from Sandvik K.K.
SUS447J1: Shomac 30 available from Showa Denko K.K.
Hastelloy B, Monel and Carpenter 20: available from Mitsubishi Materials Corporation.

The corrosion speeds of the alloys used in examples are all far lower than 0.05 mm/year, showing a high corrosion resistance. By using a distillation apparatus having its liquid-contact portion made of such alloys, the recovery of ammonia by the distillation of the aqueous solution containing ammonia, carbon dioxide and hydrogen cyanide can be continued for a long period of time and the nitrile compound can be produced by the ammoxidation stably for a long period of time.

On the other hand, Hastelloy B, Monel, pure Ti, etc., which are generally recognized as being corrosion-resistant, suffered from heavy corrosion under the severe conditions for distilling the aqueous solution containing ammonia, carbon dioxide and hydrogen cyanide.

As described above, by using a distillation apparatus having its liquid-contact portion made of the alloy 1 or alloy 2, the recovery of ammonia by the distillation of the aqueous solution containing ammonia, carbon dioxide and hydrogen cyanide can be continued for a long period of time. This enables the stable, continuous production of the nitrile compound by the ammoxidation for a long period of time. The recovered ammonia is reused in the production of the nitrile compound by the ammoxidation of the cyclic hydrocarbon or heterocyclic compound each having one or more organic substituents.

What is claimed is:

1. A method of recovering ammonia from an aqueous solution containing ammonia, carbon dioxide and hydrogen cyanide, which comprises a step of distilling the aqueous solution using a distillation apparatus in which at least a portion of the apparatus being brought into contact with the aqueous solution is made of Hastelloy C or an alloy equivalent thereto comprising 3% by weight or more of molybdenum, 15% by weight or more of nickel and 15% by weight or more of chromium,
   wherein the aqueous solution contains 5 to 50% by weight of ammonia, 0.1 to 5% by weight of hydrogen cyanide, and 1 to 20% by weight of carbon dioxide.

2. The method according to claim 1, wherein the portion of the apparatus which is brought into contact with the aqueous solution, made of the Hastelloy C or alloy equivalent thereto, is brought into contact with an aqueous solution heated to 90° or more.

3. The method according to claim 1, wherein a portion of the apparatus at which evaporation and condensation of the aqueous solution constantly occur is made of the Hastelloy C or an alloy equivalent thereto.

4. The method according to claim 1, wherein the distillation is performed at a pressure of 0.1 to 0.7 MPaG.

5. The method according to claim 1, wherein at least a part of water discharged from a bottom of the distillation apparatus is reused for absorbing ammonia, carbon dioxide and hydrogen cyanide.

6. The method according to claim 1, wherein a distilled fraction from a top of the distillation apparatus is partially condensed and a rest thereof is discharged from the distillation apparatus in a state of gas.

7. The method according to claim 1, wherein the aqueous solution is obtained by allowing a cyclic hydrocarbon or a heterocyclic compound each having at least one organic substituent to react with ammonia to obtain a reaction product gas comprising a nitrile compound, separating a produced nitrile compound from the reaction product gas, and then, allowing ammonia, carbon dioxide and hydrogen cyanide in a remaining gas to be absorbed by water.

8. The method according to claim 7, wherein the cyclic hydrocarbon is xylene and the nitrile compound is dicyanobenzene.

9. A method of producing a nitrile compound which comprises:
   a step of allowing a cyclic hydrocarbon or a heterocyclic compound each having at least one organic substituent to react with ammonia to obtain a reaction product gas comprising a nitrile compound;

a step of separating the nitrile compound from the reaction product gas, leaving a remaining gas;

a step of allowing ammonia, carbon dioxide and hydrogen cyanide in the remaining gas to be absorbed by water; and a step of recovering ammonia by the method as described in claim 1.

10. The method according to claim 9, wherein the recovered ammonia is reused in a reaction with the cyclic hydrocarbon or the heterocyclic compound.

11. The method according to claim 9, wherein the cyclic hydrocarbon is xylene and the nitrile compound is dicyanobenzene.

12. The method according to claim 1, wherein the Hastelloy C or alloy equivalent thereto comprises 3-25% by weight of molybdenum, 15-82% by weight of nickel, and 15-30% by weight of chromium.

13. The method according to claim 1, wherein the Hastelloy C or alloy equivalent thereto comprises 3.5-20% by weight of molybdenum, 15-70% by weight of nickel, and 15-25% by weight of chromium.

14. The method according to claim 1, wherein the Hastelloy C or alloy equivalent thereto further comprises a balance iron.

* * * * *